United States Patent [19]
Neely

[11] Patent Number: 6,117,445
[45] Date of Patent: Sep. 12, 2000

[54] METHODS FOR THE PREVENTION AND TREATMENT OF FIBROSIS AND SCLEROSIS

[75] Inventor: Constance F. Neely, Raleigh, N.C.

[73] Assignee: Link Technology Inc., Research Triangle Park, N.C.

[21] Appl. No.: 09/224,534

[22] Filed: Dec. 31, 1998

Related U.S. Application Data

[60] Provisional application No. 60/072,896, Jan. 28, 1998.

[51] Int. Cl.$^7$ .............................. A61F 13/02; A61F 2/02; A61K 9/48; A61K 9/20; A61L 9/04
[52] U.S. Cl. ........................... 424/434; 424/45; 424/423; 424/427; 424/435; 424/443; 424/449; 424/451; 424/464
[58] Field of Search .................................... 424/423, 427, 424/434, 435, 449, 451, 464, 45

[56] References Cited

U.S. PATENT DOCUMENTS

| | | | |
|---|---|---|---|
| 5,320,962 | 6/1994 | Stiles et al. | 435/252.3 |
| 5,571,846 | 11/1996 | Murad et al. | 514/620 |
| 5,604,199 | 2/1997 | Funanage | 514/6 |
| 5,645,839 | 7/1997 | Chobanian et al. | 424/400 |

FOREIGN PATENT DOCUMENTS

| | | |
|---|---|---|
| WO 94/03173 | 2/1994 | WIPO. |
| WO 95/26728 | 10/1995 | WIPO. |
| WO98/19541 | 5/1998 | WIPO. |
| WO98/22465 | 5/1998 | WIPO. |
| WO9967239 | 12/1999 | WIPO. |

OTHER PUBLICATIONS

Wang et al, "Extracellular ATP and ADP stimulate proliferation of Porcine aortic Smooth Muscle Cells", J. Cell. Physiol., 153(2), 221–33, 1992.
Eidelman et al.; $A_1$ adenosine–receptor antagonists activate chloride efflux from cystic fibrosis cells, Proc. Natl. Acad. Sci. USA 89:5562–5566 (1992).
Hansen et al.; The distribution of single $P_{2x1}$–receptor clusters on smooth muscle cells in relation to nerve varicosities in the rat urinary bladder, Journal of Neurocytology 27:529–539 (1998).
Spedding et al.; Developments in Purine and Pyridimidine Receptor–Based Therapeutics, Drug Development Research 39:436–441 (1996).
Ahmed et al.; Presence of Both $A_1$ and $A_{2a}$ Adenosine Receptors in Human Cells and their Interaction; *Biochemical and Biophysical Research Communications*, 208(2):871–878 (1995).
Cook et al.; Adenosine and Adenine Nucleotides Inhibit the Autonomous and Epidermal Growth Factor–Mediated Proliferation of Cultured Human Keratinocytes, *J. Invest. Dermatol*, 104:976–981 (1995).
Cronstein, B.; Adenosine, an endogenous anti–inflammatory agent, *J. Appl. Physiol.* 76(1):5–13 1994.
Dubey et al.; Exogenous and Endogenous Adenosine Inhibits Fetal Calf Serum–Induced Growth of Rat Cardiac Fibroblasts, *Circulation*; 96:2656 (1997).
Ethier et al.; Adenosine stimulates proliferation of human endothelial cells in culture; *Am. J. Physiol.* 265(Heart Circ. Physiol. 34):H131 (1993).
Fereydoun et al.; Inhibition of TNF–alpha expression by adenosine, *J. Immunology*, 156:3435 (1996).
Li et al.; The Effects of LPS and probucol on interleukin 1 (IL–1) and platelet–derived growth factor (PDGF), *Biochem Biophys. Acta*, 1225:271 (1994).
Liao et al.; Endotoxin: Possible roles in initiation and development of atherosclerosis, *J. Lab. Clin. Med.*, 128(5):452 (1996).
Mancini et al.; An interleukin–1 receptor antagonis decreases fibrosis induced by dimethylnitrosamine in rat liver; *Virchows Archiv*; 424:25–31 (1994).
Montesinos et al.; Wound healing is accelerated by Agonists of A2 Receptors, *J. Exp. Med.*; 186:1615 (1997).
Neely et al.; $P_{2x}$ purinoceptors in the feline pulmonary vascular bed: distribution and selective in vivo pharmacological probes; *Am. J. Physiol*; 270 (Lung Cell. Mol. Physiol.):L889–L897 (1996).
Neely et al.; A adenosine receptor antagonistsblock ischemia–reperfusion injury of the lung, *Am. J. Physiol.*, 268 (Lung Cell. Mol. Physiol.):L1036–L1046 (1995).
Neely et al.; $A_1$–adenosine receptor antagonists block endotoxin–induced lung injury, *Am. J. Physiol.*, 272 (Lung Cell Mol. Physiol. 16):L353–L361 (199&).
Neely et al.; $A_1$ Adenosine Receptor Antagonists Block Ischemia–Reperfusion Injury of the Heart; *Circulation* 94: (Suppl II): II–376–II–380 (1996).
Salmon et al.; Human Mononuclear Phagocytes Express Adenosine $A_1$ Receptors, *J. Immunology*, 151:2775–2785 (1993).
Thornton et al.; Both in vitro and in vivo irradiation are associated with induction of macrophage–derived fibroblast growth factors, *Clin. Exp. Immunol.* 103:67–73 (1996).

*Primary Examiner*—Carlos Azpuru
*Attorney, Agent, or Firm*—Myers Bigel Sibley & Sajove

[57] ABSTRACT

Methods of treating or preventing fibrosis and sclerosis by the administration of compositions containing $A_1$ adenosine receptor antagonists and/or $P_{2x}$ purinoceptor antagonists, or combinations thereof.

23 Claims, No Drawings

METHODS FOR THE PREVENTION AND TREATMENT OF FIBROSIS AND SCLEROSIS

This application is a continuation of U.S. provisional application No. 60/072,896; filed Jan. 28, 1998.

FIELD OF THE INVENTION

The present invention relates to methods of treating fibrosis and sclerosis, using $A_1$ adenosine receptor antagonists and $P_{2X}$ purinoceptor antagonists, or combinations thereof.

BACKGROUND

Purinergic receptors can be classified into the $P_1$ (adenosine) receptors and the $P_2$ (adenosine 5' triphosphate) receptors. Adenosine receptors can further be delineated into major subclasses, the $A_1$, $A_2$ ($A_{2a}$ and $A_{2b}$) and $A_3$ adenosine receptors. These subtypes are differentiated by molecular structure, radioligand binding profiles, and by pharmacological activity and signal transduction mechanisms. Binding of adenosine, a naturally occurring nucleoside, to specific adenosine receptors leads to either stimulation ($A_2$-receptor activation) or inhibition ($A_1$-receptor activation) of adenylate cyclase activity resulting in an increase or decrease of intracellular cAMP, respectively. Most tissues and cell types possess either the $A_1$ or $A_2$ receptor, or both. Moreover, $A_1$ adenosine receptors have been identified in the nuclear fraction of splenocytes (Donnabella, *Life Sci.* 46:1293 (1990)). Specific $A_1$, $A_2$, and $A_3$ adenosine receptor antagonists and agonists are known. See, e.g., Trivedi et al., *Structure-Activity Relationships of Adenosine $A_1$ and $A_2$ Receptors, In: Adenosine and Adenosine Receptors*, M. Williams, Ed., Humana Press, Clifton, N.J., USA (1990); Jacobson et al., *J. Medicinal Chem.* 35:407 (1992); Fredholm et al., *Pharm. Rev.* 46:143 (1994); Jacobson, *Abstracts from Purines '96, Drug Dev. Res.*, March 1996, page 112. Divalent ions ($Mg^{2+}$ and $Ca^{2+}$) and allosteric enhancers enhance the binding of $A_1$ adenosine receptor agonists to $A_1$ adenosine receptors (Kollias-Baker, *Circ. Res.* 75:961 (1994)). Allosteric enhancers enhance $A_1$ receptor mediated responses and are described in Bhattacharya, *Biochim. Biophys. Acta* 1265:15 (1995).

Based on potency profiles of structural analogues for ATP, ATP-sensitive (P2) purinoceptors have been subclassified into $P_{2X}$ and $P_{2Y}$ purinoceptors. With few exceptions, $P_{2X}$ receptors are located on vascular smooth muscle cells and mediate vasoconstriction and $P_{2Y}$ receptors are located on endothelial cells and mediate vasodilation. Burmstock and Kennedy, *Gen. Pharmacol.* 16:433 (1985; Ralevic eta 1., *Br. J. Phannacol.* 103:1108 (1991). $P_{2X}$ receptors are present on arteries of a number of different species. Bo and Burnstock, *J Vas Res* 30:87 (1993). The presence of $P_{2X}$ purinoceptors on pulmonary arteries is reported in Neely, C. F., *Am J Physiol* 270:L889–L897, 1996.

Inflammatory cells, including monocytes and alveolar macrophages express the $A_1$, $A_2$ and $A_3$ adenosine receptor subtypes. Eppell et al., *J. Immunology* 143:4141 (1989); Lapin and Whaley, *Clin. Exp. Immnunol.* 57:454 (1984); Saijadi, et al., *J. Immunol.* 156:3435 (1996). The presence of $A_1$ adenosine receptors on human monocytes/macrophages is reported, e.g., in Salmon, J. E., *J Immunology* 151:2775–2785, 1993. Mature monocytes enter the circulatory system from the bone marrow; some monocytes enter tissues and develop into macrophages in the spleen, lymph nodes, liver, lung, thymus, peritoneum, nervous system, skin and other tissues. Monocytes and macrophages can be identified by morphology, cell surface antigens, and the presence of characteristic enzymes. Both monocytes and macrophages play a role in inflammatory responses and secrete various proteins active in immune and inflammatory responses, including Tumor Necrosis Factor (TNF) and Interleukin I (IL-1)). Upon stimulation, monocytes and macrophages can generate various oxygen metabolites, including superoxide anion and $H_2O_2$ that are toxic to both pathogens and normal cells.

Fibroblasts are the major cell type responsible for the synthesis of collagen, a fibrous protein essential for maintaining the integrity of the extracellular matrix found in the dermis of the skin and other connective tissues. The production of collagen is a finely regulated process, and its disturbance may lead to the development of tissue fibrosis. The formation of fibrous tissue is part of the normal healing process after injury, including injury due to surgery. However, in some circumstances there is an abnormal accumulation of fibrous material such that it interferes with the normal function of the affected tissue.

Scar tissue serves only a structural role, but does not contribute to the function of the organ in which it appears. For example, as fibrotic scar tissue replaces heart muscle damaged by hypertension, the heart becomes less elastic and thus less able to do its job. Similarly, pulmonary fibrosis causes the lungs to stiffen and impairs lung function. Fibrotic growth can proliferate and invade healthy surrounding tissue, even after the original injury heals. In most cases fibrosis is a reactive process, and several different factors can apparently modulate the pathways leading to tissue fibrosis. Such factors include the early inflammatory responses, local increase in fibroblast cell populations, modulation of the synthetic function of fibroblasts, and altered regulation of the biosynthesis and degradation of collagen.

Stimulation of fibroblast activity is involved in the development of fibrotic conditions, including spontaneous and induced conditions. Abnormal accumulation of collagen in the extracellular matrix, resulting from excessive fibroblast proliferation and/or collagen production, can cause fibrosis of a number of tissues including the skin. Many common debilitating diseases, such as liver cirrhosis and pulmonary fibrosis, involve the proliferation of fibrous tissue as do certain skin diseases such as scleroderma, and the formation of adhesions, keloids, and hypertrophic scars.

SUMMARY OF THE PRESENT INVENTION

We have identified that fibrosis and/or sclerosis is associated with activation of $A_1$ adenosine receptors, and that administration of an $A_1$ adenosine receptor antagonist offers potential as an antifibrotic or antisclerotic treatment. The present invention accordingly provides a method of inhibiting fibrosis and/or sclerosis in a subject afflicted with a fibrosing or sclerosing disorder. The method comprises administering to the subject an effective fibrosis-inhibiting or sclerosis-inhibiting amount of an $A_1$ adenosine receptor antagonist.

We have identified that fibrosis and/or sclerosis is associated with activation of $P_{2X}$ purinoceptors, and that administration of a $P_{2X}$ purinoceptor antagonist offers potential as an antifibrotic or antisclerotic treatment. The present invention - accordingly provides a method of inhibiting fibrosis and/or sclerosis in a subject afflicted with a fibrosing or sclerosing disorder. The method comprises administering to the subject an effective fibrosis-inhibiting or sclerosis-inhibiting amount of a $P_{2X}$ purinoceptor antagonist.

The present invention further provides a method of inhibiting fibrosis and/or sclerosis in a subject afflicted with a fibrosing or sclerosing disorder, by administering an effective fibrosis-inhibiting or sclerosis-inhibiting amount of a composition containing at least one $A_1$ adenosine receptor antagonist and at least one $P_{2X}$ purinoceptor antagonist.

A first aspect of the present invention is a method of treating fibrosis or sclerosis in a subject in need of such treatment, by administering a composition containing an $A_1$ adenosine receptor antagonist, a $P_{2X}$ purinoceptor antagonist, or a combination of at least one $A_1$ adenosine receptor antagonist and at least one $P_{2X}$ purinoceptor antagonist. The composition is administered in an amount that is effective in reducing the rate of fibrosis or sclerosis that would occur without treatment.

A further aspect of the present invention is a method of preventing fibrosis or sclerosis in a subject in need of such treatment, by administering a composition containing an $A_1$ adenosine receptor antagonist, a $P_{2X}$ purinoceptor antagonist, or a combination of at least one $A_1$ adenosine receptor antagonist and at least one $P_{2X}$ purinoceptor antagonist. The composition is administered in an amount that is effective in reducing the formation of fibrotic or sclerotic tissue that would otherwise occur without treatment.

The foregoing and other objects and aspects of the present invention are explained in detail in the specification set forth below.

DETAILED DESCRIPTION

It has now been found that administration of compositions containing $A_1$ adenosine receptor antagonists and/or $P_{2X}$ purinoceptor antagonists, or a combination thereof, can prevent or inhibit fibrosis and/or sclerosis.

Endothelial injury is often due to non-infectious injurious agents, such as trauma or burns, exposure to drugs or chemical agents, immune-complex events, and ischemia-initiated events. Such injury, and the associated acute inflammatory response, is characterized by infiltration of neutrophils, adhesion of neutrophils to endothelial cells, hemorrhage, and the presence of macrophages. However, the exact mechanism by which these injurious agents induce endothelial injury is unknown. The neutrophil-derived release of reactive oxygen species may induce lipid peroxidation of biological membranes, and has been associated with an increase in collagen synthesis. Casini, *Hepatology* 25:361 (1997). The release of reactive oxygen species, and byproducts of lipid peroxidation may also promote the activation, migration, and adhesion of neutrophils to endothelial cells, and may prime macrophages for the release of cytokines and growth factors (cytokines include interleukin-1 (Il -1), interleukin-2 (Il -2), interleukin-6 (IL-6), and tumor necrosis factor-α (TNF-α); growth factors include transforming growth factor-beta (TGF-β), insulin-like growth factor-I (IGF-I), and platelet-derived growth factors (PDGFs)). It has been reported that these growth factors are elevated in disease states associated with fibrosis and/or sclerosis, and may be, in part, responsible for the fibrosis and/or sclerosis.

It is known that lipopolysaccharide (LPS, endotoxin) binds to cells and induces the release of mediators from neutrophils, monocytes, macrophages, and endothelial cells. These mediators are important in the pathophysiology of endotoxin-induced acute lung injury. The present inventor has found that, in pulmonary arterial endothelial cells, both $A_1$ adenosine receptor agonists and endotoxin (LPS) induce thromboxane release, that endotoxin induced inhibition of adenylate cyclase or thromboxane release is blocked by a highly selective $A_1$ adenosine receptor antagonist (1,3 dipropyl-8-cyclopentylxanthine (DPCPX)), and that endotoxin displaces the binding of highly selective $A_1$ adenosine receptor antagonist radioligands [$^3$H] DPCPX and $^{125}$I-BW A844U. These findings indicate that LPS binds to and activates $A_1$ adenosine receptors on pulmonary artery endothelial cells. Also, $A_1$ adenosine receptor antagonists are able to block such endotoxin-induced lung injury, supporting that activation of $A_1$ adenosine receptors is important in endotoxin-induced acute lung injury. Neely, *Am J. Physiol., Lung Cell Mol. Physiol.*, 268:L1036, 1995. In the lung, LPS produced injury is characterized by the presence of neutrophils, macrophages and red blood cells in alveoli, and by alveolar edema and necrosis. Selective $A_1$ adenosine receptor antagonists are effective in preventing LPS-induced lung injury (Neely, *Am J Physiol* 272:L353 (1997).

The present inventor has determined that $A_1$ adenosine receptors and $P_{2X}$ purinoceptors are also implicated in the pathogenesis of fibrosis and sclerosis. The present methods utilize $A_1$ adenosine receptor antagonists or $P_{2X}$ purinoceptor antagonists, or combinations thereof, to block the cellular release of factors that act in the pathogenesis of fibrosis and/or sclerosis.

The present invention provides methods of preventing and treating fibrosis and sclerosis, wherein an effective amount of an $A_1$ adenosine receptor antagonist, a $P_{2X}$ purinoceptor antagonist, or a combination thereof, is administered to a subject in need of such treatment. A single compound that antagonizes both the $A_1$ receptor and the $P_{2X}$ purinoceptor may also be used in the methods of the present invention. An effective amount is that amount able to reduce the amount of fibrotic or sclerotic growth that would occur in the absence of said antagonists, or slow the progress (over time) of fibrosis or sclerosis compared to that which would occur in the absence of said antagonists. In other words, the term "effective amount" refers to a concentration of an $A_1$ adenosine receptor antagonist, $P_{2X}$ purinoceptor antagonist, or combination thereof, which is sufficient to interfere with the progression of fibrotic or sclerotic pathological changes. Preferably, the $A_1$ adenosine receptor antagonist is a selective $A_1$ adenosine receptor antagonist. Preferably, the $P_{2X}$ purinoceptor antagonist is a selective $P_{2X}$ purinoceptor antagonist.

Disease states characterized by acute and chronic inflammation and progressive fibrosis or sclerosis include autoimmune diseases (rheumatoid arthritis, Crohn's disease, scleroderma, glomerulonephritis, and progressive systemic sclerosis); irradiation induced fibrosis; fibrosis of the heart following myocardial infarction or ischemia-reperfusion injury; fibrosis of the lung associated with adult respiratory distress syndrome, irradiation injury, immune-complex disease, inhalation of chronic irritants, or chemotherapeutic agents; cirrhosis of the liver; chronic graft rejection of transplanted organs; fibrosis of the skin following thermal exposure; gingival periodontal fibrosis; cataract formation; keloid and adhesion formation following surgery and trauma; and arteriosclerosis/atherosclerosis. Okada, *Acta Pathologica Japonica* 43:160 (1993); Nishi *Br J Ophthalmology* 80:63 (1996); Kuroki Br *J Rheumatology* 34:31 (1995); Nakao *J Dental Res* 74:1072 (1995); Herman *Clinical Nephrology* 46:34 (1996); Thornton *Clin Exp Immunology* 103:67 (1996); Garner *J Investigative Dermatology* 101:875 (1993); Salmon-Her *Archives of Dermatology* 132:802 (1996); Liao *J Lab Clin Med* 128:452 (1996).

Fibrosis is the formation of fibrous tissue, usually as a reparative or a reactive process. As used herein, "fibrosis"

does not refer to the formation of fibrous tissue that is a normal part of an organ or tissue, but includes those disorders or disease states that are caused by or accompanied by the abnormal deposition of scar tissue. Fibrosis can follow surgery in the form of adhesions, keloid tumors or hypertrophic (very severe) scarring. Fibrosis causes contractures and joint dislocation following severe burns, wounds or orthopedic injuries; it can occur in any organ and accompanies many disease states, such as hepatitis (liver cirrhosis), hypertension (heart failure), tuberculosis (pulmonary fibrosis), scleroderma (fibrotic skin and internal organs), diabetes (nephropathy) and atherosclerosis (fibrotic blood vessels). Fibrosis also includes all arteriosclerotic disorders, pulmonary fibrosis, adult respiratory distress syndrome, inflammatory disorders including autoimmune disorders, sclerodermas, cirrhosis, keloids, adhesions and hypertrophic scars.

Keloids are firm, non-encapsulated, usually linear mass of hyperplastic scar tissue. Keloids comprise relatively large and fairly parallel bands of densely collagenous material, separated by bands or cellular fibrous tissue. Keloids commonly occur in the dermis and adjacent subcutaneous tissue, often after a traumatic injury, surgery or a burn. Keloids may be surgically removed, but often recur at the same site after surgical removal.

Sclerosis refers to an induration or hardening of chronic inflammatory origin. Hyperplasia of the interstitial fibrous or glial connective tissue can lead to induration of nervous system structures.

Skeletal muscle fibrosis is a phenomenon which frequently occurs in diseased or damaged muscle. It is characterized by the excessive growth of fibrous tissue, and impairs muscle function. The amount of muscle function loss generally increases with the extent of fibrosis. Disorders which typically result in skeletal muscle fibrosis include, for example, muscular dystrophies, such as Duchenne's muscular dystrophy and Becker's muscular dystrophy; and neuromuscular diseases, such as acute polyneuritis, poliomyelitis, Werdig/Hofftnan disease, amyotrophic lateral sclerosis, and progressive bulbar atrophy. Such conditions also include traumatic denervation atrophy induced by either trauma or by neuromuscular disorders. Skeletal muscle fibrosis is often progressive. The present invention provides a method of treating skeletal muscle fibrosis in subjects, preferably mammals, in need of such treatment. The method is effective for reducing the extent of, or preventing the progression of, skeletal muscle fibrosis in a subject suffering from a disorder which targets skeletal muscle tissue. The treatment includes administering to the individual a pharmaceutical composition containing an $A_1$ adenosine receptor antagonist, a $P_{2X}$ purinoceptor antagonist, or a combination thereof, in an amount effective to reduce the rate of skeletal muscle fibrotic tissue growth.

Cardiovascular disease states involving fibrosis that can be treated by the methods of the present invention include left ventricular hypertrophy secondary to hypertension; and fibrosis associated with myocardial infarction, myocarditis, or with ischemia-reperfusion injury to the heart. The present invention provides a method of treating cardiac muscle fibrosis or cardiovascular fibrosis (e.g., arteriosclerotic changes in coronary arteries) in subjects in need of such treatment. The treatment includes administering to the individual a pharmaceutical composition containing an $A_1$ adenosine receptor antagonist, a $P_{2X}$ purinoceptor antagonist, or a combination thereof, in an amount effective to reduce the rate of cardiac muscle fibrotic tissue growth, or arteriosclerotic or fibrotic changes in the vasculature.

Dermal fibrosing disorders include, but are not limited to, scleroderma, morphea, keloids, hypertrophic scars, familial cutaneous collagenoma, and connective tissue nevi of the collagen type. The present invention provides a method of treating dermal fibrosis in subjects in need of such treatment. The method is effective for reducing the extent of, or preventing the progression of, dermal fibrosis. The treatment includes administering to the individual a pharmaceutical composition containing an $A_1$ adenosine receptor antagonist, a $P_{2X}$ purinoceptor antagonist, or a combination thereof, in an amount effective to reduce the rate of dermal fibrotic tissue growth. Administration may include topical or transdermal administration or injection into the affected area.

Fibrosis of internal organs (e.g., liver, lung, kidney, heart, blood vessels, gastrointestinal tract), occurs in disorders such as pulmonary fibrosis, liver cirrhosis, and scar formation. The present invention provides a method of treating fibrosis in internal organs in subjects in need of such treatment. The method is effective for reducing the extent of, or preventing the progression of, fibrotic changes in the target organ. The treatment includes administering to the individual a pharmaceutical composition containing an $A_1$ adenosine receptor antagonist, a $P_{2X}$ purinoceptor antagonist, or a combination thereof, in an amount effective to reduce the rate of internal organ fibrotic tissue growth. Administration may vary depending on the target organ, e.g., aerosol inhalation may be used to treat pulmonary fibrosis, whereas parenteral administration may be used to treat fibrosis of the liver.

Fibrotic conditions of the eye include conditions such as diabetic retinopathy, postsurgical scarring (for example, after glaucoma filtering surgery), and proliferative vitreoretinopathy. The present invention provides a method of treating opthalmic fibrosis in subjects in need of such treatment. The method is effective for reducing the extent of, or preventing the progression of, fibrotic changes in the eye. The treatment includes administering to the individual a pharmaceutical composition containing an $A_1$ adenosine receptor antagonist, a $P_{2X}$ purinoceptor antagonist, or a combination thereof, in an amount effective to reduce the rate of ophthalmic fibrotic tissue growth. Treatment may include intra-ocular administration or topical administration of the active compound.

In rheumatoid arthritis, a characteristic feature is persistent inflammatory synovitis of the peripheral joints, leading to cartilage destruction and bone erosions. Rheumatoid synovitis is characterized by an increased number of synovial lining cells and perivascular infiltration with mononuclear cells. Activated synovial fibroblasts are common, particularly at the interface of bone and cartilage. The rheumatoid synovium is characterized by the presence of cytokines, chemokines and other products secreted by activated lymphocytes, macrophages, and fibroblasts. Bone and cartilage destruction occurs in juxtaposition to the inflamed synovium, or pannus, that spreads to cover the articular cartilage. The present invention provides a method of treating rheumatoid arthritis in subjects in need of such treatment. The method is effective for reducing the extent of, or preventing the progression of, articular damage. The treatment includes administering to the individual a pharmaceutical composition containing an $A_1$ adenosine receptor antagonist, a $P_{2X}$ purinoceptor antagonist, or a combination thereof, in an amount effective to ameliorate symptoms or reduce the rate of articular damage. Treatment may include intra-articular administration of the active compound to a specific affected joint.

The phrase "fibrotic disorder" or "sclerotic disorder" means diseases, conditions or other abnormal medical states which typically result in fibrosis or sclerosis, respectively. The phrase "suffering from" such a disorder means that the subject exhibits symptoms of an aforementioned disorder and thus is likely to develop significant pathological fibrosis or sclerosis in the course of events, even though signs of fibrosis or sclerosis may not be evident at the time of diagnosis. The diagnosis of individuals who suffer from disorders that typically result in debilitating fibrosis or sclerosis may be readily made by those having ordinary skill in the art using well established criteria and methods.

The range of dosages and the frequency of delivery of a composition according to the present invention, to be effective in treating or preventing fibrosis or sclerosis, can be determined by those having ordinary skill in the art. A methodology for determining appropriate dosage in treating skeletal muscle fibrosis, for example, includes determining the existing state of skeletal muscle fibrosis of a patient; administering at a preselected frequency, a preselected amount of pharmaceutical formulation containing $A_1$ adenosine receptor antagonists and/or $P_{2X}$ purinoceptor antagonists; determining the state of skeletal muscle fibrosis exhibited by the patient at a later time when the disorder, if untreated, would have increased fibrotic tissue development; and adjusting the dosage amount and/or delivery rate to reduce, maintain or increase the effect of preventing or reducing fibrosis. A number of methods are available to determine the state of skeletal muscle fibrosis of a patient, including evaluating a muscle tissue biopsy from the subject by histochemical or immuno-histochemical stains that can detect fibrotic tissue. Examples of histochemical stains include, for example, hematoxylin and eosin (H & E), trichrome and ATPase (at pH 4.3, 4.65 and 10.4). Representative antibodies that can be used to label muscle fibers for immuno-histochemical staining include, for example, myosin, type IV collagen, laminin, and fibronectin.

Subjects to be treated by the method of the present invention include, but are not limited to, subjects afflicted with a dermal fibrosing disorder, a skeletal muscle fibrosing disorder, fibrosis of an internal organ, cardiovascular fibrosis, fibrosis due to autoimmune disease, and fibrotic conditions of the eye.

Subjects to be treated by the method of the present invention include both human and animal (e.g., dog, cat, cow, horse) subjects, and are preferably mammals. Subjects include those diagnosed with a fibrosing or sclerosing disorder, in which it is desired to inhibit, prevent or reduce fibrotic or sclerotic changes. Subjects also include those scheduled to undergo surgery, where the methods may be employed prophylactically (prior to surgery or following surgery, but prior to the occurrence of fibrosis or sclerosis), e.g., to prevent or reduce keloid, adhesion, or hypertrophic scar formation.

Effective dosages of the active compounds in the present methods will vary depending on the subject to be treated (body weight, age, general health), route and timing of administration, type of formulation, characteristics of the compounds used, the severity of disease, concurrent therapies, and the desired effect. These amounts can be determined by pharmacokinetic principles well known to those skilled in the art.

Agents which bind to $A_1$ adenosine receptors are well known to those of skill in the art. One of the best known classes of adenosine receptor antagonists are the xanthines, which include caffeine and theophylline. See e.g., Müller et al., *J. Med. Chem.* 33:2822 (1990). Both agonists and antagonists have been synthesized for $A_1$ adenosine receptors. For example, 1,3-dipropyl-8-cyclopentylxanthine (DPCPX) is a highly selective $A_1$ adenosine receptor antagonist with negligible nonspecific binding (less than 1%) in tissues (Jacobson et al., *J. Med. Chem.* 35:407 (1992); Bruns, RF "Adenosine Receptor Binding Assays", *Receptor Biochemistry and Methodology. Volume II: Adenosine Receptors,* DMF Cooper and C. Londos (Eds.), Alan Liss, Inc., New York, N.Y. 1988, pp. 43–62). Other examples of $A_1$ adenosine receptor antagonists include, but are not limited to, xanthine amine congener (XAC); xanthine carboxylic congener (XCC); 1,3-dipropyl-xanthines such as 1,3-dipropyl-8-(-3-noradamantyl) xanthine (KW 3902), 1,3-dipropyl-8-(dicyclopropylmethyl) xanthine (KF 15372), 1,3-dipropyl-8-[2-(5,6-epoxy)norbonyl]xanthine (ENX), 8-(1-aminocyclopentyl)-1,3-dipropylxanthine (IRFI 117), 1,3-dipropyl-8-(3-noradamantyl) xanthine (NAX) and 1,3-dipropyl-8-(3-oxocyclopentyl) xanthine (KFM 19); 1-propyl-3-(4-amino)-3-phenethyl)-8-cyclopentylxanthine (BW-A844U); 1,3-dipropyl-8-sulfophenylxanthine (DPSPX); cyclopentyl theophylline (CPT) and 7-[2-ethyl (2-hydroxyethyl)amino]-ethyl]-3,7-dihydro-1,3-dimethyl-8-(phenylmethyl)-1H-purine-2,6-dione (Bamifylline); $N^6$, 9-methyl adenines such as (±)-$N^6$-endonorbornan-2-yl-9-methyladenine (N-0861) and 8-(N-methylisopropyl) amino-$N^6$- (5'-endohydroxy-endonorbornyl)-9-methyladenine (WRC-0571); $N^6$, 9-disubstituted adenines; 2-phenyl-7-deazaadenines such as (R)-7,8-dimethyl-2-phenyl-9-(1-phenylethyl)-7-deazaadenine; 7,8-dihydro-8-ethyl-2-(3-noradamantyl)-4-propyl-1H-imidazo[2,1-i]purin-5(4H)-one; (±)R-1-[(,)-3[2-[phenylpyrazolo (1,5-a) pyridin-3-yl] acryloyl]-2-piperidine ethanol; 8-azaxanthines such as 7-cyclopentyl-1,3-dipropyl-8-azaxanthine; tetrahydrobenzothiophenones such as ethyl-3-(benzylthio)-4-oxo-4,5,6,7-tetrahydrobenzo[c]thiophene-1-carboxylate; N-6-cyclopentyl-3'-substituted xylofuranosyl adenosines (Van Calinbergh, *J. Med. Chem.* 40:3765, November 1997).

Additionally, selective analogues of adenosine receptor antagonists have been developed through the "functionalized congener" approach. Analogues of adenosine receptor ligands bearing functionalized chains have been synthesized and attached covalently to various organic moieties such as amines and peptides. Jacobson et al. *J. Med. Chem.* 35:408 (1992) has proposed various derivatives of adenosine and theophylline for use as receptor antagonists.

Antibodies raised against the $A_1$ adenosine receptor that selectively target and bind to this receptor can also be used as $A_1$ adenosine receptor antagonists. Such antibodies targeted to the $A_1$ adenosine receptor can be produced routinely in accordance with well known methods of antibody production. As used herein, the term "$A_1$ adenosine receptor antagonist" encompasses antibodies that selectively or specifically bind to the receptor, when such antibodies are used for their antagonist effects.

$P_{2X}$ purinoceptor antagonists are known in the art; an example of a selective $P_{2X}$ purinoceptor antagonist is pyridoxalphosphate-6-azophenyl-2',4'-disulfonic acid (PPADS). Additional specific pharmacological antagonists of purinoceptors have been described by Humphrey et al., *Naunyn-Schmied. Arch. Pharmacol.* 352:585 (1995); Abracchio and Burnstock, *Pharmac. Ther.* 64:445 (1994); Bultmann et al., *Naunyn-Schmied. Arch. Pharmacol.* 354:481 (1996); and Bultrann et al., *Naunyn-Schmied. Arch. Pharmacol.* 354:498 (1996). Antibodies raised against the $P_{2X}$ purinoceptor that selectively target and bind to this receptor can also be used as $P_{2X}$ purinoceptor antagonists. Such antibodies targeted to the $P_{2X}$ purinoceptor can be produced routinely in accordance with well known methods of antibody production. As used herein, the term "$P_{2X}$ purinoceptor antagonist" encompasses antibodies that selectively or specifically bind to the receptor, when such antibodies are used for their antagonist effects.

As used herein, an amount of a compound that is effective for treating fibrosis and/or sclerosis is that which: inhibits the further progression of fibrotic or sclerotic changes that would otherwise occur; that which reduces the rate of fibrosis or sclerosis; or that which prevents fibrosis or sclerosis from occurring. Compositions of $A_1$ receptor antagonists and $P_{2X}$ purinoceptor antagonists used in the present methods may further comprise a pharmaceutically acceptable carrier, including but not limited to saline, water, dextrose and water, cyclodextrins or similar sugar solutions, low dose sodium hydroxide solutions, propylene glycol, and polyethylene glycol.

The pharmaceutical composition may be employed, as an example, in oral dosage form as a liquid composition. Such liquid compositions can include suspension compositions or syrup compositions and can be prepared with such carriers as water; a saccharide such as sucrose, sorbitol, fructose, and the like; a glycol such as polyethyleneglycol, polypropyleneglycol, and the like; an oil such as sesame oil, olive oil, soybean oil, and the like; an antiseptic such as p-hydroxybenzoic acid esters and the like; and a flavor component such as a fruit flavor or a mint flavor. The pharmaceutical composition may also be in the form of powder, pills, capsules, and tablets and can be prepared with various carriers. Suitable carriers include, but are not limited to, lactose, glucose, sucrose, mannitol, and the like; disintegrators such as starch, sodium alginate, and the like; binders such as polyvinyl alcohol, hydroxypropyl cellulose, gelatin, and the like; surfactants such as, for example, fatty acid esters; and plasticizers such as, for example, glycerins. It should be noted that in the preparation of the tablets and capsules, a solid pharmaceutical carrier is used. The pharmaceutical composition may be used in the form of an aerosol where advantageous, such as in the treatment of pulmonary fibrosis.

The pharmaceutical compositions also may be formulated as an injectable solution. These compositions are prepared using appropriate sterile aqueous solutions which may include, but are not limited to, water, saline, dextrose and water or other similar sugar solutions, and buffer additives, as will be apparent to one skilled in the art.

The formulations of the present invention further include those suitable for topical or transdermal administration, ophthalmic, parenteral (including subcutaneous, intramuscular and intravenous), oral, inhalational, or nasal administration. Topical formulations comprise the active compound dissolved or suspended in one or more media such as mineral oil, petroleum, polyhydroxy alcohols or other bases used for topical pharmaceutical formulations. The addition of other accessory ingredients may also be desirable. Ophthalmic formulations comprise purified aqueous solutions of the active compounds with preservative agents and isotonic agents. The formulations are preferably adjusted so that the pH and isotonic factors match that of the eye.

It is to be understood that the choice of formulation may vary depending on the specific compound utilized. The formulations may conveniently be presented in unit dosage form and may be prepared by any of the methods well known in the art of pharmacy.

Pharmaceutical compositions that include $A_1$ adenosine receptor antagonists and/or $P_{2X}$ purinoceptor antagonists may be administered by any method that can deliver the composition to the site in the body of a subject where anti-fibrotic or anti-sclerotic treatment is desired. These methods include but are not limited to oral, subcutaneous, transdermal, inhalational or aerosol, intravenous, intramuscular, intra-articular, intra-thecal, liposomal and parenteral methods of administration. In order to treat fibrosis confined to a specific site, a site-specific method of delivery is preferred, such as infusion directly to an organ. For example, to treat fibrosis associated with denervation atrophy caused by traumatic injury to one or a group of nerves affecting muscles in a localized region of the body, delivery of the pharmaceutical composition directly to the affected muscles, such as by intramuscular injection, may be used to advantage. Methods of administering compositions in a site-specific manner will vary depending on the affected site. Appropriate methods of site-specific delivery will be readily apparent to one skilled in the art. When fibrosis is associated with disease that affects tissues throughout the body, a systemic delivery method, such as intravenous infusion or subcutaneous delivery is desirable.

The following examples are provided to illustrate the present invention, and should not be construed as limiting thereof.

EXAMPLE 1

Effect of $A_1$ Adenosine Receptor Antagonist on Experimentally Induced Liver Fibrosis in Rats Hepatic fibrosis is induced in a group of male Spague Dawley rats by intraperitoneal injection of dimethylnitrosamine, as is known in the art (e.g., 1% DMN dissolved in saline solution at 10 mg/kg/day for 3 consecutive days per week for 2 weeks, for rats of 150–200 g body weight).

Animals are divided into three groups: Group A animals receive DMN (10 mg/kg/day) for 3 consecutive days a week for 2 weeks. This dose and treatment schedule with DMN is reported to produce hepatic fibrosis; Mancini, *Virchows Archiv* 424:25–31, 1994.

Group B animals receive the $A_1$ adenosine receptor antagonist (±) N6-(endo-2-Norbornyl)-9-methyladenine (N0861) as an intravenous bolus (2 mg/kg) prior to DMN exposure, plus as a continuous infusion of N0861 (0.02 mg/kg/min) at the time DMN treatment is begun and continued for 2 weeks. The continuous intravenous infusion may be achieved, e.g., via a mini osmotic pump inserted under the skin of the back. See Peck and Cusack, *Drugs of the Future* 18:433–435, 1993.

Group C animals receive only N0861 as a bolus (2 mg/kg) plus a continuous infusion of N0861 (0.02 mg/kg/min) for 2 weeks and are a control group.

After 2 weeks, animals are sacrificed and the livers removed. Hepatic fibrosis is quantitated using methods as known in the art, e.g., 1) a quantitative colorimetric assay for collagen; 2) immunohistochemistry-immunoperoxidase staining for alpha-SM actin and for laminin; and/or 3) histomorphometric analysis of inflammatory infiltrate and fibrosis. Mancini, *Virchows Archiv* 424:25–31, 1994.

Following sacrifice, resident peritoneal macrophages in each rat are isolated and cultured protein levels of PDGF-AA, PDGF-BB, and TGF-beta 1 are determined using techniques available in the art, such as by inmrunoblot analysis. Kovacs, *Immunobiology* 190:263–274, 1994.

EXAMPLE 2

Effect of $P_{2X}$ Purinoceptor Antagonist on Experimentally Induced Liver Fibrosis in Rats Hepatic fibrosis is induced in a group of male Spague Dawley rats as described in example 1 above. Animals are divided into three treatment groups.

The P$_{2X}$ purinoceptor antagonist pyridoxalphosphate-6-azophenyl-2',4'-disulfonic acid (PPADS) is administered as an intravenous bolus (15 mg/kg) every 4 hours.

Group A animals receive DMN (10 mg/kg/day) for 3 consecutive days a week for 2 weeks. This dose and treatment schedule with DMN is known to produce hepatic fibrosis. Mancini, *Virchows Archiv* 424:25–31, 1994.

Group B animals receive PPADS as an intravenous bolus (15 mg/kg) every 4 hours at the time DMN treatment is begun, and for 2 weeks thereafter.

Group C animals receive only PPADS as an intravenous bolus (15 mg/kg) every 4 hours for 2 weeks and represent the control group.

After 2 weeks, animals are sacrificed and their livers removed. Hepatic fibrosis is quantitated using methods known in the art, such as 1) a quantitative calorimetric assay for collagen; 2) immunohistochemistry-immunoperoxidase staining for alpha-SM actin and for laminin; and/or 3) histomorphometric analysis of inflammatory infiltrate and fibrosis. Mancini *Virchows Archiv* 424:25–31, 1994.

Also following sacrifice, resident peritoneal macrophages are isolated from each animal and cultured protein levels of PDGF-AA, PDGF-BB, and TGF-beta 1 are determined using techniques available in the art, such as by immunoblot analysis. Kovacs, *Immunobiology* 190:263–274, 1994.

EXAMPLE 3

Effect of Combined A$_1$ Adenosine Receptor Antagonist and P$_{2X}$ Purinoceptor Antagonist on Experimentally Induced Liver Fibrosis in Rats Hepatic fibrosis is induced in male Spague Dawley rats as described above.

Each animal receives the A$_1$ adenosine receptor antagonist, (±) N6-(endo-2-Norbornyl)-9-methyladenine (N0861) administered as an intravenous bolus (2 mg/kg) and as a continuous intravenous infusion (0.02 mg/kg/min); each animal additionally receives the P$_{2X}$ purinoceptor antagonist pyridoxalphosphate-6-azophenyl-2',4'-disulfonic acid (PPADS) as an intravenous bolus (15 mg/kg) every 4 hours, at the time DMN treatment is begun. Animals are divided into three treatment groups.

Group A animals receive DMN (10 mg/kg/day) for 3 consecutive days a week for 2 weeks. This dose and treatment schedule with DMN is reported to produce hepatic fibrosis. Mancini, *Virchows Archiv* 424:25–31, 1994.

Group B animals receive N0861 as an intravenous bolus (2 mg/kg) plus as a continuous intravenous infusion (0.02 mg/kg/min), and receive PPADS (15 mg/kg) every 4 hours at the time DMN treatment is begun and continued for 2 weeks.

Group C animals receive only N0861 as a bolus (2 mg/kg) plus a continuous intravenous infusion (0.02 mg/kg/min) plus PPADS (15 mg/kg) every 4 hours for 2 weeks and represent the control group.

After 2 weeks, animals are sacrificed and their livers removed. Hepatic fibrosis will be quantitated with the use of 1) a quantitative colorimetric assay for collagen; 2) inimunohistochemistry-immunoperoxidase staining for alpha-SM actin and for laminin; and 3) histomorphometric analysis of inflammatory infiltrate and fibrosis. Mancini, R., *Virchows Archiv* 424:25–31, 1994.

Also, following sacrifice resident peritoneal macrophages will be isolated and cultured protein levels for PDGF-AA, PDGF-BB, and TGF-beta 1 will be determined with the use of immunoblot analysis. Kovacs, E. J., *Immunobiol* 190:263–274, 1994.

EXAMPLE 4

Effect of A$_1$ Adenosine Receptor Antagonist on Experimentally Induced Arteriosclerotic Changes in Pigs Domestic pigs are sedated, anesthetized, intubated and ventilated using techniques that are known in the art. Under aseptic conditions, a left thoracotomy is performed and the proximal segments of the left anterior descending (LAD) and circumflex coronary artery (LCX) are carefully dissected. The dissected segments are gently wrapped with cotton mesh soaked in 0.05 ml suspension of recombinant human IL-β (2.5 μg) bound to sepharose beads. This technique is reported to produce arteriosclerotic changes in coronary arteries in pigs; Ito, *J Clin Invest* 96:1288–1294, 1995.

Animals are divided into 3 treatment groups. In Group A animals, the coronary arteries are treated with cotton mesh soaked in 0.05 ml suspension of recombinant human IL-β (2.5 μg) bound to sepharose beads.

In Group B animals, prior to the thoracotomy, an A$_1$ adenosine receptor antagonist, (±) N6-(endo-2-Norbornyl)-9-methyladenine (N0861) is administered as an intravenous bolus (2 mg/kg) plus as a continuous intravenous infusion (0.02 mg/kg/min). After the continuous intravenous infusion is started, the thoracotomy as described above is performed, and the coronary arteries are dissected and treated with cotton mesh soaked in 0.05 ml suspension of recombinant human IL-μ(2.5 μg) bound to sepharose beads. The continuous infusion of N0861 is maintained for two weeks.

In Group C, animals receive only N0861 bolus (2 mg/kg) plus a continuous infusion of N0861 (0.02 mg/kg/min) for 2 weeks.

After 2 weeks the animals are sacrificed and the hearts are removed. The coronary arteries are fixed by perfusion with saline and 6% formaldehyde. After fixation the arteries are cut transversely into segments at approximately 5-mm intervals and these segments are stained for photomicroscopy to quantitate the degree of intimal thickening. See, e.g., Ito, *J Clin Invest* 96:1288–1294, 1995. In addition to quantitating intimal thickening of these segments, protein levels for PDGF-AA, PDGF-BB, and TGF-beta 1 are determined using immunoblot analysis as is known in the art (see Kovacs, *Immunobiol* 190:263–274, 1994).

EXAMPLE 5

Effect of P$_{2X}$ Purinoceptor Antagonist on Experimentally Induced Arteriosclerotic Changes in Pigs Arteriosclerotic changes in coronary arteries in pigs are produced as described above. The pigs are divided into three treatment groups.

In Group A animals, coronary arteries are treated with cotton mesh soaked in 0.05 ml suspension of recombinant human IL-β (2.5 μg) bound to sepharose beads.

In Group B animals, prior to the thoracotomy, the P$_{2X}$ purinoceptor antagonist pyridoxalphosphate-6-azophenyl-2',4'-disulfonic acid (PPADS) is administered as an intravenous bolus (15 mg/kg) every 4 hours for 2 weeks. After administration of PPADS is begun, the thoracotomy is performed, and the coronary arteries are dissected and treated with cotton mesh soaked in 0.05 ml suspension of recombinant human IL-β (2.5 μg) bound to sepharose beads.

In Group C, animals receive only PPADS as an intravenous bolus (15 mg/kg) every 4 hours for 2 weeks and represent the control group.

After 2 weeks the animals are sacrificed and the hearts are removed. The coronary arteries are perfused with saline and 6% formaldehyde. After fixation the arteries are cut transversely into segments at 5-mm intervals and these segments are stained for photomicroscopy to quantitate the degree of intimal thickening. Ito, *J Clin Invest* 96:1288–1294, 1995. In addition to quantitating intimal thickening of these segments, protein levels for PDGF-AA, PDGF-BB, and TGF-beta 1 are determined using immunoblot analysis. See, e.g., Kovacs, *Immunobiol* 190:263–274, 1994.

EXAMPLE 6

Effect of Combined $A_1$ Adenosine Receptor Antagonist and $P_{2X}$ Purinoceptor Antagonist on Experimentally Induced Arteriosclerotic Changes in Pigs Arteriosclerotic changes are induced in domestic pigs' arteries as described above. The pigs are divided into three treatment groups.

In Group A animals, coronary arteries are treated with cotton mesh soaked in 0.05 ml suspension of recombinant human IL-β (2.5 μg) bound to sepharose beads.

In Group B animals, prior to the thoracotomy, an $A_1$ adenosine receptor antagonist, (±) N6-(endo-2-Norbornyl)-9-methyladenine (N0861) is administered as an intravenous bolus (2 mg/kg) plus as a continuous intravenous infusion (0.02 mg/kg/min); the $P_{2X}$ purinoceptor antagonist pyridoxalphosphate-6-azophenyl-2',4'-disulfonic acid (PPADS) is also administered as an intravenous bolus (15 mg/kg) every 4 hours for 2 weeks. Following the start of N0861 and PPADS administration, the thoracotomy is performed, and the coronary arteries are dissected and treated with cotton mesh soaked in 0.05 ml suspension of recombinant human IL-β(2.5 μg) bound to sepharose beads.

In Group C, animals receive N0861 as a bolus (2 mg/kg) plus as a continuous intravenous infusion (0.02 mg/kg/min); and also receive PPADS (15 mg/kg) every 4 hours for 2 weeks. These animals are the control group.

After 2 weeks the animals are sacrificed and the hearts are removed. The coronary arteries are perfused with saline and 6% formaldehyde. After fixation the arteries are cut transversely into segments at 5-mm intervals and these segments are stained for photomicroscopy to quantitate the degree of intimal thickening. Ito, *J Clin Invest* 96:1288–1294, 1995. In addition to quantitating intimal thickening of these segments, protein levels for PDGF-AA, PDGF-BB, and TGF-beta 1 is determined with the use of immunoblot analysis. Kovacs, *Immunobiol* 190:263–274, 1994.

EXAMPLE 7

Experimentally Induced Dermal Fibrosis in Mice

Human keloids are implanted in athymic mice to create an animal model of human keloids. See Waki et al., *Arch. Otolaryngol. Head Neck Surg.* 117:1177 (1991). Mice are divided into four treatment groups and keloids are measured. One group is administered an $A_1$ adenosine receptor antagonist, by injection into the keloid or by topical or transdermal administration. A second group is treated with an identical regime, but using a $P_{2X}$ purinoceptor antagonist. A third group is treated with an identical regime, but using a combination of the $A_1$ adenosine receptor antagonist and the $P_{2X}$ purinoceptor antagonist. A fourth group is maintained as a control group, receiving either no treatment, or treatment with a placebo.

After treatment is concluded, keloids are assessed by measurement, biopsy and autopsy to determine the rate of growth or rate of regression of keloids.

That which is claimed is:

1. A method of treating a disorder that results in fibrosis or sclerosis, in a subject in need of such treatment, comprising administering to said subject a composition selected from the group consisting of:
   (a) $A_1$ adenosine receptor antagonists;
   (b) $P_{2X}$ purinoceptor antagonists; and
   (c) a combination of at least one $A_1$ adenosine receptor antagonist and at least one $P_{2X}$ purinoceptor antagonist;
   wherein said composition is administered in an amount effective to reduce the rate of fibrosis or sclerosis.

2. The method of claim 1 wherein said disorder is selected from skeletal muscle fibrosis, irradiation-induced fibrosis, autoimmune-related fibrosis, cardiovascular fibrosis, arteriosclerotic disorders, pulmonary fibrosis, adult respiratory distress syndrome, inflammatory disorders, scleroderma, cirrhosis, keloids, adhesions and hypertrophic scars.

3. A method of claim 1 wherein said disorder is skeletal muscle fibrosis associated with a condition selected from muscular dystrophy, denervation atrophy induced by neuromuscular disease, and traumatic injury-induced denervation atrophy.

4. A method according to claim 1 wherein said disorder is cardiovascular fibrosis selected from left ventricular hypertrophy secondary to hypertension, fibrosis associated with myocardial infarction, fibrosis associated with ischemiareperfusion injury, and fibrosis associated with myocarditis.

5. A method according to claim 1, wherein said disorder is a dermal fibrosis.

6. A method according to claim 1, wherein said disorder is selected from keloid formation, hypertrophic scar formation, or adhesion formation.

7. A method according to claim 1, wherein said disorder is an ophthalmic fibrosis.

8. A method according to claim 1, wherein said composition is administered topically.

9. A method according to claim 1, wherein said composition is administered parenterally.

10. A method according to claim 1, wherein said disorder is a dermal fibrosis and said composition is administered topically.

11. A method according to claim 1, wherein said disorder is pulmonary fibrosis and said composition is administered by inhalation.

12. A method according to claim 1, wherein said disorder is rheumatoid arthritis and said composition is administered by intra-articular injection.

13. A method according to claim 1, wherein said composition is administered directly to the affected anatomic site.

14. A method according to claim 1, wherein said composition is administered prophylactically.

15. A method according to claim 1, wherein said $A_1$ adenosine receptor antagonist is an antibody that binds to the $A_1$ adenosine receptor.

16. A method according to claim 1, wherein said $P_{2X}$ purinoceptor antagonist is an antibody that binds to the $P_{2X}$ purinoceptor.

17. A method of preventing fibrosis or sclerosis in a subject in need of such treatment, comprising administering to said subject a composition selected from the group consisting of:

(a) $A_1$ adenosine receptor antagonists;

(b) $P_{2X}$ purinoceptor antagonists; and (c) a combination of at least one $A_1$ adenosine receptor antagonist and at least one $P_{2X}$ purinoceptor antagonist;

wherein said composition is administered in an amount effective to reduce the formation of fibrotic or sclerotic tissue that would occur in the absence of such treatment.

18. A method according to claim 17, wherein said fibrosis or sclerosis is due to keloid formation, hypertrophic scar formation, or adhesion formation.

19. A method according to claim 17, wherein said fibrosis is pulmonary fibrosis.

20. A method according to claim 19, wherein said pulmonary fibrosis is due to adult respiratory distress syndrome or irradiation induced fibrosis.

21. A method according to claim 17, wherein said composition is administered prior to scheduled surgery.

22. A method according to claim 17, wherein said $A_1$ adenosine receptor antagonist is an antibody that binds to the $A_1$ adenosine receptor.

23. A method according to claim 17, wherein said $P_{2X}$ purinoceptor antagonist is an antibody that binds to the $P_{2X}$ purinoceptor.

* * * * *

UNITED STATES PATENT AND TRADEMARK OFFICE
CERTIFICATE OF CORRECTION

PATENT NO.      : 6,117,445
DATED           : September 12, 2000
INVENTOR(S)     : Neely It is certified that error appears in the above-identified patent and that said Letters Patent is hereby corrected as shown below:

<u>Title page,</u>
Item [56], OTHER PUBLICATIONS, second entry for Neely et al. delete "A adenosine" and replace with -- $A_1$ adenosine --
*Attorney, Agent, or Firm*, delete "Sajove" and replace with -- Sajovec --

Signed and Sealed this

Eleventh Day of June, 2002

Attest:

Attesting Officer

JAMES E. ROGAN
*Director of the United States Patent and Trademark Office*